(12) United States Patent
Akerlund et al.

(10) Patent No.: US 10,806,668 B2
(45) Date of Patent: Oct. 20, 2020

(54) METHOD AND ASSEMBLY FOR FLUID TRANSFER AND DRUG CONTAINMENT IN AN INFUSION SYSTEM

(71) Applicant: Carmel Pharma AB, Gothenburg (SE)

(72) Inventors: Roger Akerlund, Gothenburg (SE); Kjell Andreasson, Vastra Frolunda (SE); Petri Horppu, Gothenburg (SE)

(73) Assignee: Carmel Pharma AB, Gothenburg (SE)

( * ) Notice: Subject to any disclaimer, the term of this patent is extended or adjusted under 35 U.S.C. 154(b) by 135 days.

(21) Appl. No.: 16/156,374

(22) Filed: Oct. 10, 2018

(65) Prior Publication Data

US 2019/0038506 A1 Feb. 7, 2019

Related U.S. Application Data

(62) Division of application No. 14/023,650, filed on Sep. 11, 2013, now Pat. No. 10,123,938, which is a
(Continued)

(51) Int. Cl.
*A61J 1/20* (2006.01)
*A61J 1/14* (2006.01)
(Continued)

(52) U.S. Cl.
CPC ............ *A61J 1/2089* (2013.01); *A61J 1/1406* (2013.01); *A61J 1/1425* (2015.05); *A61J 1/1481* (2015.05);
(Continued)

(58) Field of Classification Search
CPC ... A61J 1/2096; B65D 41/325; A61M 39/221; A61M 2039/222
See application file for complete search history.

(56) References Cited

U.S. PATENT DOCUMENTS 1,844,342 A 2/1932 Berman
2,010,417 A 8/1935 Schwab
(Continued)

FOREIGN PATENT DOCUMENTS

AU 200112863 B2 5/2001
DE 2005519 A1 10/1971
(Continued)

OTHER PUBLICATIONS

Taiwan Search Report for Taiwan Appln 092106323 dated Mar. 21, 2003, 4 pgs.
(Continued)

*Primary Examiner* — Timothy P. Kelly
(74) *Attorney, Agent, or Firm* — Servilla Whitney LLC (57) ABSTRACT

A fluid transfer assembly, drug container, and method for enabling fluid transfer in an infusion system is taught. The assembly includes a fluid container containing an infusion fluid, and a drug container. The fluid container has at least one inlet port for receiving a medical substance from the drug container. The assembly further includes at least one fluid barrier controlling fluid passage between the drug container and the fluid container. The inlet port exhibits a first luer-lock connector, and the drug a container is sealed by a cap exhibiting a second luer-lock connector for attachment to the first luer-lock connector. The fluid barrier is designed and arranged to be ruptured by an external force to allow the fluid passage.

8 Claims, 4 Drawing Sheets

Related U.S. Application Data division of application No. 10/063,159, filed on Mar. 26, 2002, now Pat. No. 8,562,583.

(51) Int. Cl.
  *A61M 5/14* (2006.01)
  *A61M 39/04* (2006.01)
  *A61M 39/22* (2006.01)

(52) U.S. Cl.
  CPC .......... *A61J 1/2096* (2013.01); *A61M 5/1409* (2013.01); *A61J 1/1468* (2015.05); *A61J 1/201* (2015.05); *A61J 1/2034* (2015.05); *A61J 1/2055* (2015.05); *A61M 39/045* (2013.01); *A61M 2039/222* (2013.01)

(56) References Cited

U.S. PATENT DOCUMENTS

| | | | |
|---|---|---|---|
| 2,697,438 A | 12/1954 | Hickey | |
| 2,717,599 A | 9/1955 | Huber | |
| 3,064,651 A | 11/1962 | Henderson | |
| 3,071,135 A | 1/1963 | Baldwin et al. | |
| 3,308,822 A | 3/1967 | De Luca | |
| 3,316,908 A | 5/1967 | Burke | |
| 3,340,671 A | 9/1967 | Loo | |
| 3,390,677 A | 7/1968 | Razimbaud | |
| 3,448,740 A | 6/1969 | Figge | |
| 3,542,240 A | 11/1970 | Solowey | |
| 3,783,895 A | 1/1974 | Weichselbaum | |
| 3,788,320 A | 1/1974 | Dye | |
| 3,822,700 A | 7/1974 | Pennington | |
| 3,938,520 A | 2/1976 | Scislowicz et al. | |
| 3,976,073 A | 8/1976 | Quick et al. | |
| 4,296,786 A | 10/1981 | Brignola | |
| 4,296,860 A | 10/1981 | Hsu et al. | |
| D270,568 S | 9/1983 | Armstrong | |
| 4,490,139 A | 12/1984 | Huizenga et al. | |
| 4,493,348 A * | 1/1985 | Lemmons ............. | A61J 1/2096 138/109 |
| 4,516,976 A | 5/1985 | Bell | |
| 4,573,967 A | 3/1986 | Hargrove et al. | |
| 4,576,211 A | 3/1986 | Valentini et al. | |
| 4,581,016 A | 4/1986 | Gettig | |
| 4,582,223 A | 4/1986 | Kobe | |
| 4,588,403 A | 5/1986 | Weiss et al. | |
| 4,600,040 A | 7/1986 | Nashlund | |
| 4,623,343 A | 11/1986 | Thompson | |
| 4,629,455 A | 12/1986 | Kanno | |
| 4,632,673 A | 12/1986 | Tiitola et al. | |
| 4,636,204 A | 1/1987 | Christopherson et al. | |
| 4,673,400 A | 6/1987 | Martin | |
| 4,673,404 A | 6/1987 | Gustavsson | |
| 4,737,150 A | 4/1988 | Baeumle et al. | |
| 4,752,287 A | 6/1988 | Kurtz et al. | |
| 4,759,756 A | 7/1988 | Forman et al. | |
| 4,768,568 A | 9/1988 | Fournier et al. | |
| 4,792,329 A | 12/1988 | Schreuder | |
| 4,804,015 A | 2/1989 | Albinsson | |
| 4,822,340 A | 4/1989 | Kamstra | |
| 4,826,492 A | 5/1989 | Magasi | |
| 4,834,717 A | 5/1989 | Haber et al. | |
| 4,842,585 A | 6/1989 | Witt | |
| 4,850,978 A | 7/1989 | Dudar et al. | |
| 4,864,717 A | 9/1989 | Baus, Jr. | |
| 4,872,494 A | 10/1989 | Coccia | |
| 4,878,897 A | 11/1989 | Katzin | |
| 4,889,529 A | 12/1989 | Haindl | |
| 4,898,209 A | 2/1990 | Zbed | |
| 4,909,290 A | 3/1990 | Coccia | |
| 4,932,937 A | 6/1990 | Gustavsson et al. | |
| 4,944,736 A | 7/1990 | Holtz | |
| 4,964,855 A | 10/1990 | Todd et al. | |
| 4,982,769 A | 1/1991 | Fournier et al. | |
| 4,994,048 A | 2/1991 | Metzger | |
| 4,997,083 A | 3/1991 | Loretti et al. | |
| 5,017,186 A | 5/1991 | Arnold | |
| 5,041,105 A | 8/1991 | D'Alo et al. | |
| 5,061,264 A | 10/1991 | Scarrow | |
| 5,071,413 A | 12/1991 | Utterberg | |
| 5,122,116 A | 6/1992 | Kriesel et al. | |
| 5,122,123 A | 6/1992 | Vaillancourt | |
| 5,137,524 A | 8/1992 | Lynn et al. | |
| 5,158,554 A | 10/1992 | Jepson et al. | |
| 5,176,673 A | 1/1993 | Marrucchi | |
| 5,199,947 A | 4/1993 | Lopez et al. | |
| 5,201,725 A | 4/1993 | Kling | |
| 5,207,658 A | 5/1993 | Rosen et al. | |
| 5,232,109 A | 8/1993 | Tirrell et al. | |
| 5,254,097 A | 10/1993 | Schock et al. | |
| 5,279,576 A | 1/1994 | Loo et al. | |
| 5,279,583 A | 1/1994 | Shober, Jr. et al. | |
| 5,279,605 A | 1/1994 | Karrasch et al. | |
| 5,308,347 A | 5/1994 | Sunago et al. | |
| 5,312,366 A | 5/1994 | Vailancourt | |
| 5,328,480 A | 7/1994 | Melker et al. | |
| 5,342,347 A | 8/1994 | Kikuchi et al. | |
| 5,344,163 A | 8/1994 | Sinnett | |
| 5,356,406 A | 10/1994 | Schraga | |
| 5,368,586 A * | 11/1994 | Van Der Heiden ... | A61J 1/2089 604/403 |
| 5,385,545 A | 1/1995 | Kriesel et al. | |
| 5,385,547 A | 1/1995 | Wong et al. | |
| 5,389,085 A | 2/1995 | D'Alessio et al. | |
| 5,405,326 A | 4/1995 | Haber et al. | |
| 5,445,630 A | 8/1995 | Richmond | |
| 5,447,501 A | 9/1995 | Karlsson et al. | |
| 5,456,675 A | 10/1995 | Wolbring et al. | |
| 5,470,522 A | 11/1995 | Thome et al. | |
| 5,478,328 A | 12/1995 | Silverman et al. | |
| 5,478,337 A | 12/1995 | Okamoto et al. | |
| 5,492,531 A | 2/1996 | Post et al. | |
| 5,514,117 A | 5/1996 | Lynn | |
| 5,515,871 A | 5/1996 | Bittner et al. | |
| 5,536,259 A | 7/1996 | Utterberg | |
| 5,575,780 A | 11/1996 | Saito | |
| 5,593,028 A | 1/1997 | Haber et al. | |
| 5,613,954 A | 3/1997 | Nelson et al. | |
| 5,632,735 A | 5/1997 | Wyatt et al. | |
| 5,647,845 A | 7/1997 | Haber et al. | |
| 5,685,866 A | 11/1997 | Lopez | |
| 5,752,942 A | 5/1998 | Doyle et al. | |
| 5,766,147 A | 6/1998 | Sancoff et al. | |
| 5,766,211 A | 6/1998 | Wood et al. | |
| 5,782,872 A | 7/1998 | Muller | |
| 5,795,336 A | 8/1998 | Romano et al. | |
| 5,817,083 A | 10/1998 | Shemesh et al. | |
| 5,820,609 A | 10/1998 | Saito | |
| 5,827,262 A | 10/1998 | Neftel et al. | |
| 5,837,262 A | 11/1998 | Golubev et al. | |
| 5,871,110 A * | 2/1999 | Grimard ................ | A61J 1/2096 215/249 |
| 5,875,931 A | 3/1999 | Py | |
| 5,879,345 A | 3/1999 | Aneas | |
| 5,879,526 A | 4/1999 | Vaillancourt | |
| 5,921,419 A * | 7/1999 | Niedospial, Jr. ...... | A61J 1/2096 215/247 |
| 5,924,584 A * | 7/1999 | Hellstrom ............. | A61J 1/2096 215/247 |
| 5,934,510 A | 8/1999 | Anderson | |
| 5,984,899 A | 11/1999 | D'Alessio et al. | |
| 6,063,068 A | 5/2000 | Fowles et al. | |
| D427,308 S | 6/2000 | Zinger | |
| 6,070,623 A | 6/2000 | Aneas | |
| 6,071,270 A | 6/2000 | Fowles et al. | |
| 6,090,091 A | 7/2000 | Fowles et al. | |
| 6,113,068 A | 9/2000 | Ryan | |
| 6,113,583 A | 9/2000 | Fowles et al. | |
| 6,142,446 A | 11/2000 | Leinsing | |
| 6,146,362 A | 11/2000 | Turnbull et al. | |
| 6,179,823 B1 | 1/2001 | Niedospial, Jr. | |
| 6,209,738 B1 | 4/2001 | Jansen et al. | |
| 6,221,065 B1 | 4/2001 | Davis | |
| 6,245,056 B1 | 6/2001 | Walker et al. | |

(56) References Cited

U.S. PATENT DOCUMENTS

| | | |
|---|---|---|
| D445,501 S | 7/2001 | Niedospial, Jr. |
| 6,253,804 B1 | 7/2001 | Safabash |
| 6,378,714 B1 | 4/2002 | Jansen et al. |
| 6,387,074 B1 | 5/2002 | Horppu et al. |
| 6,453,956 B2 | 9/2002 | Safabash |
| 6,471,674 B1 | 10/2002 | Emig et al. |
| 6,517,523 B1 | 2/2003 | Kaneko et al. |
| 6,537,263 B1 | 3/2003 | Aneas |
| 6,571,837 B2 | 6/2003 | Jansen et al. |
| 6,591,876 B2 | 7/2003 | Safabash |
| 6,644,367 B1 | 11/2003 | Savage et al. |
| 6,685,692 B2 | 2/2004 | Fathallah |
| 6,715,520 B2 | 4/2004 | Andreasson et al. |
| 6,761,286 B2 | 7/2004 | Py et al. |
| D495,416 S | 8/2004 | Dimeo et al. |
| 6,786,244 B1 | 9/2004 | Jones |
| D506,256 S | 6/2005 | Miyoshi et al. |
| 6,960,194 B2 | 11/2005 | Hommann et al. |
| 7,000,806 B2 | 2/2006 | Py et al. |
| 7,080,672 B2 | 7/2006 | Fournie et al. |
| 7,297,140 B2 | 11/2007 | Orlu et al. |
| D570,477 S | 6/2008 | Gallogly et al. |
| D572,820 S | 7/2008 | Gallogly et al. |
| D577,438 S | 9/2008 | Gallogly et al. |
| D577,822 S | 9/2008 | Gallogly et al. |
| D582,033 S | 12/2008 | Baxter et al. |
| D605,755 S | 12/2009 | Baxter et al. |
| 7,703,486 B2 | 4/2010 | Costanzo |
| D616,984 S | 6/2010 | Gilboa |
| 7,744,581 B2 | 6/2010 | Wallen et al. |
| 2001/0021825 A1 | 9/2001 | Becker et al. |
| 2001/0025671 A1 | 10/2001 | Safabash |
| 2002/0002352 A1 | 1/2002 | Becker et al. |
| 2002/0082586 A1 | 6/2002 | Finley et al. |
| 2002/0121496 A1 | 9/2002 | Thiebault et al. |
| 2002/0127150 A1 | 9/2002 | Sasso |
| 2002/0177819 A1 | 11/2002 | Barker et al. |
| 2003/0010717 A1 | 1/2003 | Brugger et al. |
| 2003/0070726 A1 | 4/2003 | Andreasson et al. |
| 2003/0106610 A1 | 6/2003 | Roos et al. |
| 2003/0107628 A1 | 6/2003 | Fowles et al. |
| 2003/0199846 A1 | 10/2003 | Fowles et al. |
| 2003/0233083 A1 | 12/2003 | Houwaert et al. |
| 2004/0116858 A1 | 6/2004 | Heinz et al. |
| 2004/0116891 A1 | 6/2004 | Curutcharry |
| 2004/0199139 A1 | 10/2004 | Fowles et al. |
| 2004/0215147 A1 | 10/2004 | Wessman et al. |
| 2005/0215977 A1 | 9/2005 | Uschold |
| 2006/0025747 A1 | 2/2006 | Sullivan et al. |
| 2006/0106360 A1 | 5/2006 | Wong |
| 2006/0111667 A1 | 5/2006 | Matsuura et al. |
| 2006/0157984 A1 | 7/2006 | Rome et al. |
| 2006/0186045 A1 | 8/2006 | Jensen et al. |
| 2007/0021725 A1 | 1/2007 | Villette |
| 2007/0060841 A1 | 3/2007 | Henshaw |
| 2007/0088313 A1 | 4/2007 | Zinger et al. |
| 2007/0106244 A1 | 5/2007 | Mosler et al. |
| 2007/0179441 A1 | 8/2007 | Chevallier |
| 2007/0270759 A1 | 11/2007 | Pessin |
| 2007/0270778 A9 | 11/2007 | Zinger et al. |
| 2008/0045919 A1 | 2/2008 | Jakob et al. |
| 2008/0103453 A1 | 5/2008 | Liversidge |
| 2008/0103485 A1 | 5/2008 | Kruger |
| 2008/0172039 A1 | 7/2008 | Raines |
| 2008/0223484 A1 | 9/2008 | Horppu |
| 2008/0287920 A1 | 11/2008 | Fangrow et al. |
| 2008/0312634 A1 | 12/2008 | Helmerson et al. |
| 2009/0254042 A1 | 10/2009 | Gratwohl et al. |
| 2010/0137827 A1 | 6/2010 | Warren et al. |
| 2010/0204671 A1 | 8/2010 | Kraushaar et al. |
| 2010/0243099 A1 | 9/2010 | Yodfat |
| 2020/0268607 A1 * | 8/2020 | Gobbi Frattini ........ A61J 1/145 |

FOREIGN PATENT DOCUMENTS

| | | |
|---|---|---|
| EP | 0255025 A1 | 2/1988 |
| EP | 0259582 A1 | 3/1988 |
| EP | 0285424 A1 | 5/1988 |
| EP | 0311787 A2 | 4/1989 |
| EP | 0376629 A2 | 7/1990 |
| EP | 0803267 A2 | 10/1997 |
| EP | 0819442 A1 | 1/1998 |
| EP | 0995453 A1 | 4/2000 |
| EP | 1060730 A2 | 12/2000 |
| EP | 1484073 A1 | 12/2004 |
| EP | 1731128 A1 | 12/2006 |
| FR | 2757405 A1 | 6/1998 |
| FR | 2780878 A1 | 1/2000 |
| GB | 1579065 A | 11/1980 |
| JP | 49-12690 B2 | 5/1972 |
| JP | 288664 | 7/1990 |
| JP | 3030963 U | 8/1996 |
| JP | 167022 | 6/2000 |
| JP | 2000167022 | 6/2000 |
| JP | 2001505092 A | 4/2001 |
| JP | 2001293085 A | 10/2001 |
| TW | 482670 B | 4/2002 |
| WO | 84/04672 A1 | 12/1984 |
| WO | 84/04673 A1 | 12/1984 |
| WO | 90/03536 A1 | 4/1990 |
| WO | 98/19724 A1 | 5/1998 |
| WO | 99/27886 A1 | 6/1999 |
| WO | 99/62578 A2 | 12/1999 |
| WO | 00/05292 A1 | 2/2000 |
| WO | 00/35517 A1 | 6/2000 |
| WO | 01/80928 A2 | 11/2001 |
| WO | 02/02048 A2 | 1/2002 |
| WO | 02/11794 A1 | 2/2002 |
| WO | 02/064077 A1 | 8/2002 |
| WO | 02/076540 A1 | 10/2002 |
| WO | 2005/074860 A1 | 8/2005 |
| WO | 2006/082350 A1 | 8/2006 |
| WO | 2006/083333 A1 | 8/2006 |
| WO | 2006/138184 A2 | 12/2006 |
| WO | 2008/115102 A1 | 9/2008 |

OTHER PUBLICATIONS

Final Office Action in U.S. Appl. No. 10/063,159, dated Apr. 1, 2013, 9 pgs.

Japanese Office Action in 2003-577789, dated Feb. 24, 2009, 4 pgs.

Japanese Office Action in No. 2003-583539, dated May 1, 2009, 3 pgs.

PCT International Search Report in PCT/EP2008/067522, dated Aug. 12, 2009, 2 pgs.

PCT International Search Report in PCT/EP2008/067535 dated Oct. 13, 2009, 3 pgs.

* cited by examiner

METHOD AND ASSEMBLY FOR FLUID TRANSFER AND DRUG CONTAINMENT IN AN INFUSION SYSTEM

CROSS-REFERENCE TO RELATED APPLICATIONS

This Application is a divisional of U.S. patent application Ser. No. 14/023,650 filed Sep. 11, 2013, now allowed, which is a divisional of U.S. patent application Ser. No. 10/063,159 filed Mar. 26, 2002, which issued as U.S. Pat. No. 8,562,583 on Oct. 22, 2013, the disclosure of which is hereby incorporated by reference in its entirety.

BACKGROUND OF INVENTION

Technical Field

The present invention relates to a fluid transfer assembly for use in an infusion system, including a fluid container containing an infusion fluid, and a drug container containing a medical substance, wherein the fluid container has at least one inlet port for receiving the medical substance from the drug container and the assembly further includes at least one fluid barrier controlling fluid passage between the drug container arid the fluid container. The invention also relates to a drug container for use in the infusion system, and to a method for enabling fluid transfer in the infusion system.

Background Information

A serious problem in connection with drug preparation, drug administration and other similar handling is the risk that medical and pharmacological staff are exposed to drugs or solvents which might escape into the ambient air. This problem Is particularly serious when cytotoxins, antiviral drugs, antibiotics and radiopharmaceuticals are concerned.

For this reason, there has been a need of safer systems for handling and administrating drugs and other medical substances.

Accordingly, U.S. Pat. No. 4,564,054 discloses a fluid transfer device for transferring a substance from one vessel to another vessel avoiding leakage of liquid and gas contaminants. The disclosed device comprises a first member designed as a hollow sleeve and having a piercing member provided with a passageway. The piercing member is attached to the first member which has a first barrier member at one end just opposite the tip of the piercing member. Thereby, the piercing member can be passed and retracted through the first barrier member which seals one end of the first member. The fluid transfer device further comprises a second member which is attached to or attachable to one of the vessels or to means arranged to communicate therewith. The second member has a second barrier member, and mating connection means arranged on the first and second members for providing a releasable locking of the members with respect to each other. The barrier members are liquid and gas-proof sealing members which seal tightly after penetration and retraction of the piercing member and prevent leakage of liquid as well as gas contaminants. In the connected position of the first and second members, the barrier members are located in such a way with respect to each other that the piercing member can be passed there through.

According to U.S. Pat. No. 4,564,054, the above-mentioned piercing member is a needle arranged for puncturing the first and the second barrier members, wherein the end opposite to the one end of the first member has means for sealingly receiving or being permanently attached to an injection syringe or the like for withdrawing and/or adding substance to the vessel attached to the second member. When attached to the first member, the injection syringe or the like communicates with the passageway of the needle, so that in the retracted position the needle is hermetically enclosed in the first member having the injection syringe or the like connected thereto.

International Patent Publication No. WO 99/27886 to Fowles et al. discloses a connector device intended for establishing fluid communication between a first container and a second container. The connector device comprises a first sleeve member having a first and a second end, wherein the first sleeve member has a first attaching member at the first end which is adapted to attach to the first container. The connector device further comprises a second sleeve member which has a first end and a second end. Thereby, the second sleeve member is associated to the first sleeve member and movable with respect thereto from an inactivated position to an activated position, wherein the second sleeve member has a second attaching member at the second end adapted to attach the second sleeve member to the second container. According to WO 99/27886, the connector device further comprises a first and second piercing member projecting from one of the first and second sleeve members for providing a fluid flow path from the first container to the second container, and means for Independently hermetically sealing the first and second members.

Furthermore, U.S. Pat. No. 6,258,078 discloses a luer connector which facilitates connection of a hypodermic syringe to a vial, comprising a luer connectable to a syringe and which extends to a sharpened end capable of being driven through a puncturable vial closure to thereby puncture the closure, a luer support mountable on a vial, and which initially supports the luer in a first position in which the sharpened end of the conduit Is pointed towards the closure, and a luer driver such that movement of the driver relative to the support causes the luer to be driven so that the sharpened end punctures the closure and enters the vial.

When performing infusion, it is often necessary to Inject a drug or other medical substance into the infusion fluid inside an infusion bag or other infusion fluid container. This is normally done by means of penetrating a septum or another fluid barrier of an injection port on the infusion bag or the infusion fluid line with a hypodermic needle of a syringe filled with the medical fluid in question.

However, it has been found that the use of regular syringes or other drug containers according to prior art when injecting hazardous substances such as cytotoxins into an infusion bag or another infusion fluid container might cause pollution of the working environment, something which of course Is unacceptable. For this reason, there is a need of an improved device which eliminates the risk that potentially health-hazardous substances escape into the ambient air or working environment when injecting a drug or another medical substance into an infusion system.

Furthermore, there is a strong need of reducing the costs for medical treatment such as infusion treatment. One way of reducing the costs would be to reduce the number of medical device components which are needed for introducing medical substances into the infusion system, and which have to be kept in stock at hospitals which perform such infusion treatment.

SUMMARY OF INVENTION

Accordingly, a first object of the present invention is to provide a very simple, reliable and safe fluid transfer assembly for use in an infusion system, which assembly allows the administration of a medical substance to a patient using a minimum of medical device components. This first object is achieved by means of a fluid transfer assembly including a fluid container containing an infusion fluid, and a drug container containing a medical substance, wherein the fluid container has at least one inlet port for receiving the medical substance from the drug container, and the assembly further includes at least one fluid barrier controlling fluid passage between the drug container and the fluid container. Thereby, the inlet port exhibits a first luer-lock connector, and the drug container is sealed by a cap exhibiting a second luer-lock connector for attachment to the first luer-lock connector, wherein the fluid barrier is designed and arranged to be ruptured by an external force to allow the fluid passage.

A second object of the present invention is to provide a drug container for use in the assembly according to the invention. This second object is achieved by means of a drug container containing a fixed dose of a medical substance, wherein the drug container is sealed by a cap exhibiting a luer-lock connector for attachment to a corresponding connector provided on an Inlet port of a container for infusion fluid In order to create a luer-lock coupling.

A third object of the present Invention is to provide a method for enabling fluid transfer in an Infusion system including the assembly according to the invention. This third object is achieved by means of a method which includes to provide a fluid container containing an infusion fluid and a drug container containing a medical substance, wherein the fluid container has at least one inlet port for receiving the medical substance from the drug container, and the method further includes to provide the infusion system with at least one fluid barrier controlling fluid passage between the drug container and the fluid container. Thereby, the method further Includes to provide the fluid container with a first luer-connector on the inlet port, to provide the drug container with a cap exhibiting a second luer-lock connector, and to attach the first luer-lock connector to the second luer-lock connector by means of a luer-lock coupling. Furthermore, the method includes to apply an external force onto said fluid barrier to open the fluid passage, to create a positive pressure inside the fluid container, to transfer at least part of the positive pressure to the drug container via the fluid passage, and to remove the positive pressure from the fluid container In order to initiate transfer of the medical substance from the drug container to the fluid container.

Further objects of the present invention will become evident from the following description, and the features enabling these further objects to be achieved are listed in the dependent claims.

BRIEF DESCRIPTION OF DRAWINGS

In the following, the present invention will be described in greater detail with reference to the attached drawings, in which.

DETAILED DESCRIPTION

In the following, a preferred embodiment and a number of alternative embodiments of the assembly according to the invention will be described in greater detail with reference to the attached FIGS. 1-5.

The fluid transfer assembly according to the invention is intended for use in an infusion system of the type where it might become necessary to introduce a medical substance, such as a drug, cytotoxin or an antibiotic, into an infusion fluid, such as a saline solution.

Figure 1:
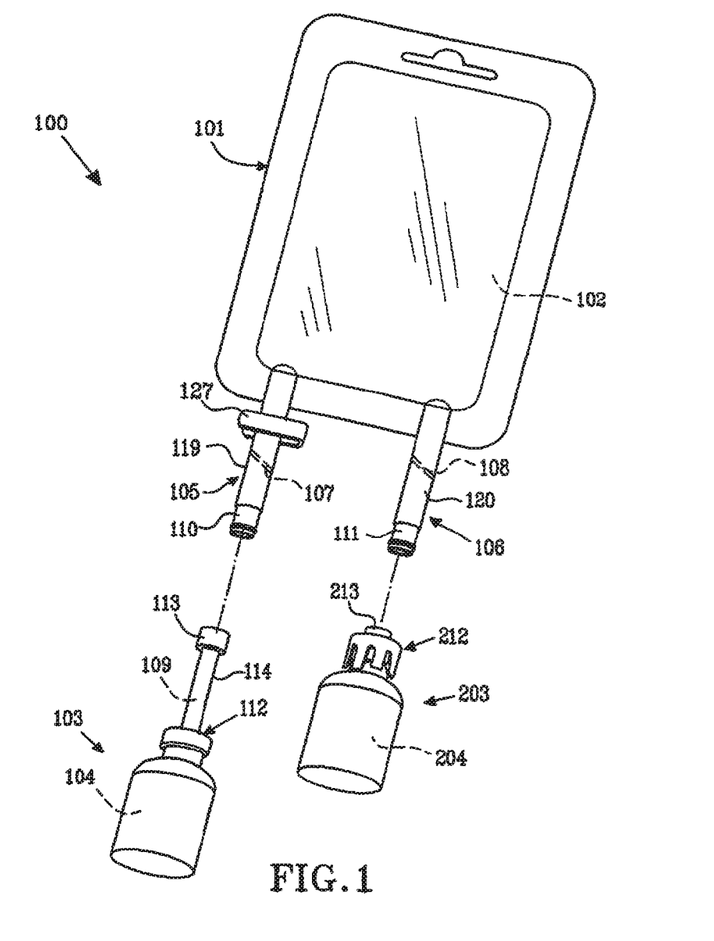
FIG. 1 is a perspective view illustrating both a preferred embodiment and an alternative embodiment of a fluid transfer assembly according to the invention.

As is evident from FIG. 1, the assembly 100 includes a fluid container 101 containing an infusion fluid 102 and a drug container 103, 203 containing a medical substance 104, 204.

Preferably, the fluid container 101 is a flexible bag made of a plastic film which exhibits suitable properties for the application. The fluid container 101 has at least one inlet port 105, 106 for receiving the medical substance 104, 204 from the drug container 103, 203. The assembly further includes at least one fluid barrier 107, 108 controlling fluid passage between the drug container 103, 203 and the fluid container 101.

It should be noted that FIG. 1 illustrates both preferred (e.g., reference numerals 101, 105 and 103) and alternative embodiments (e.g., reference numerals 101, 106 and 203) of the fluid transfer assembly according to the invention. Accordingly, in real life, only one of the ports, e.g., the one denoted 105, would act as an inlet port for receiving the medical substance from the drug container 103, whereas the other port 106 would act as an outlet port for a mixture of the infusion fluid and the introduced medical substance. Alternatively, the port denoted 106 in FIG. 1 could act as an inlet port for medical substance from the drug container 203, while the port denoted 105 could act as an outlet port to which an infusion line can be connected.

Different types of inlet ports are known per se. An inlet port according to prior art usually exhibits a septum acting as a fluid barrier. Such a septum according to the prior art is intended to be penetrated by a piercing member such as a hypodermic needle of a syringe containing the medical substance which is to be administrated.

According to the invention, however, the inlet port 105, 106 includes a first luer connector 110, 111. The function of male/female luer-lock connectors is well known per se, but for other uses than in the assembly according to the invention.

According to the invention, the drug container 103, 203 is sealed by a cap 112, 212 including a second luer-lock connector 113, 213 for attachment to the first luer-connector 110, 111. This feature of the present invention enables the drug container 103, 203 to be attached to the infusion fluid container 101 in a very simple, fast and safe way.

Furthermore, according to the invention, the fluid barrier 107, 109, 108 is designed and arranged to be ruptured by an external force to allow the fluid passage from the drug container to the fluid container, or vice versa. This feature ensures that no premature fluid communication takes place between the drug container and the fluid container.

In one advantageous embodiment of the fluid transfer assembly according to the invention, the inlet port 105, 106 forms a first fluid duct between the fluid container 101 and the first luer-lock connector 110, 111, wherein the fluid barrier 107, 108 is provided inside this first fluid duct.

Figure 2:
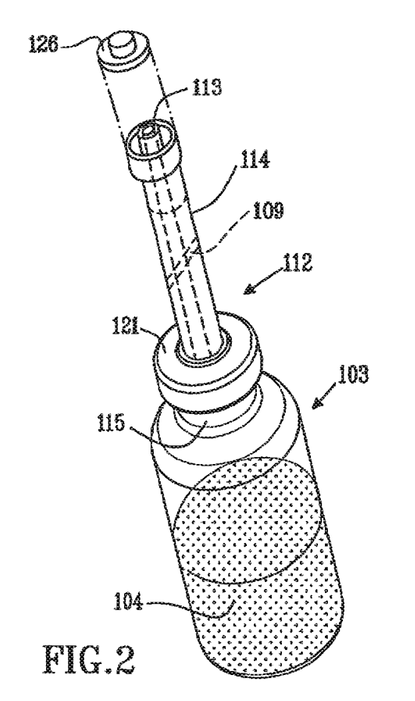
FIG. 2 is a perspective view of a drug container according to a preferred embodiment of the invention.

In another advantageous embodiment, the cap 112 of the drug container 103 includes a protruding member 114 which forms a second fluid duct between the drug container 103 and the second luer-lock connector 113, wherein the fluid barrier 109 is provided inside the second fluid duct.

In a preferred embodiment of the assembly according to the invention, the inlet port 105 forms a first fluid duct between the fluid container 101 and the first luerconnector 110. Furthermore, the cap 112 includes a protruding member 114 which forms a second fluid duct between the drug container 103 and the second luer-lock connector 113, wherein fluid barriers 107, 109 are provided both inside the first and the second fluid ducts. This feature provide full control over the fluid communication between the drug container and fluid container, and ensures that no accidental fluid transfer can take place.

Figure 3:
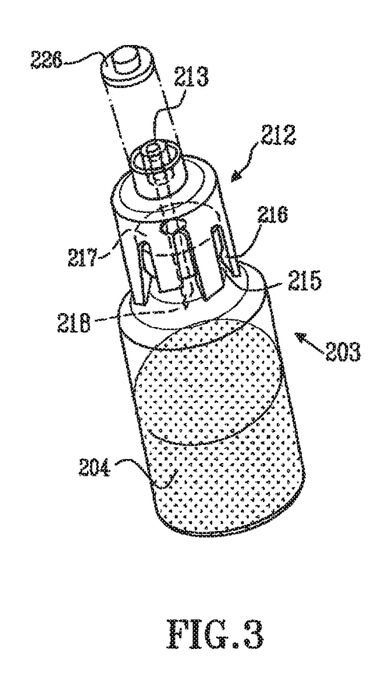
FIG. 3 is a perspective view of a drug container according to an alternative embodiment of the invention.

In an alternative embodiment of the fluid transfer assembly according to the invention, the second luer-lock connector 213 is attached directly to the cap 212. Even more advantageously, as illustrated in FIG. 3, the second luer-lock connector 213 is an integral part of the cap 212. In order to prevent contamination, as indicated in FIG. 2, and in the embodiment in FIG. 3, also in order to seal the drug container, the second luer-lock connector 113, 213 preferably is protected by a removable closure 126, 226 or a protective lid, or alternatively a pierceable closure, before use.

In the alternative embodiment of the assembly, the drug container 203 preferably includes a neck 215 as indicated in FIG. 3, wherein the cap 212 includes locking members 216 for grasping the neck 215. Even more advantageously, the drug container also includes an opening sealed by a closure 217, wherein the cap 212 includes a hollow needle 218 for penetrating the closure 217. The alternative embodiment enables the use of conventional drug vials in the assembly according to the invention, something which might be advantageous for practical reasons.

In a preferred embodiment of the fluid transfer assembly as shown in FIGS. 1 and 2, the drug container 103 includes a neck 115, wherein the cap 112 includes a protruding member 114 which is attached to the neck 115 by means of an annular capsule member 121. The capsule-like attachment makes it possible modify a fairly conventional drug vial-filling line to produce drug containers for use in the fluid transfer assembly according to the invention. However, within the scope of the invention, it is also conceivable with embodiments where a protruding member is attached to the drug container by means of another suitable permanent attachment.

Figure 4:
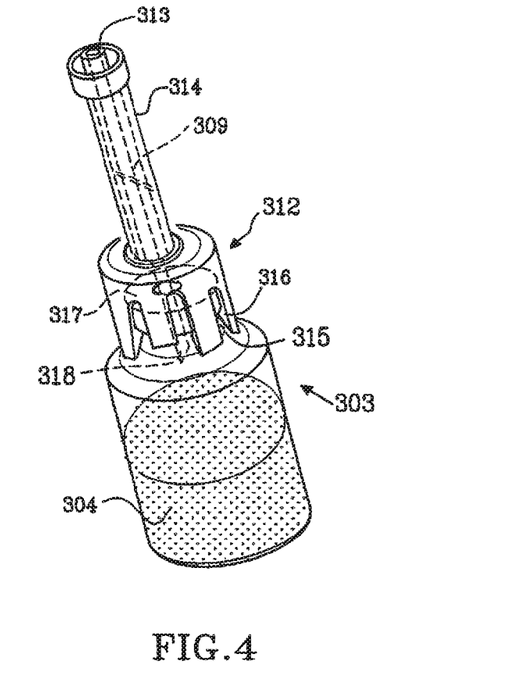
FIG. 4 is a perspective view of a drug container according to another alternative embodiment of the invention.

In another advantageous embodiment of the fluid transfer assembly according to the invention, as illustrated in FIG. 4, the drug container 303 includes a neck 315, and the cap 312 includes a protruding member 314 that forms a second fluid duct between the drug container 303 and the second luer-lock connector 313. In this embodiment the cap 312 further includes locking members 316 for grasping the neck 315. The locking members 316 enable drug vials of a conventional design to be used in the fluid transfer assembly, whereas the protruding member 314 makes it easier to control the fluid passage between the fluid container in question and the drug container 303, or vice versa.

In a preferred embodiment of the fluid transfer assembly as indicated in FIGS. 1 and 2, the fluid barrier is made of a brittle polymer member 107, 109, 108 which can be divided along a weakening line by means of the external force. However, within the scope of the invention, it is conceivable with many different designs of the fluid barrier, as long as the barrier provides a safe sealing of the fluid container and/or the drug container, and as long as it is possible for an operator to eliminate the sealing action by means of applying an external force onto the fluid barrier in order to break, rupture, puncture, or dislocate the fluid barrier and open a fluid passage through the barrier.

In another embodiment of the fluid transfer assembly, the walls 119 of the inlet port 105 are made of a flexible material and form a first fluid duct between the fluid container 101 and the first luer-lock connector 110. In this embodiment, in order to provide improved control of the fluid passage, the fluid transfer assembly 100 further includes a first clamping member 127 for compressing the walls 119, closing the first fluid duct and preventing undesired fluid passage between the fluid container 101 and the first luer-lock connector 110. This embodiment is particularly valuable after having transferred the entire fixed dose of medical substance from the drug container into the infusion fluid container, since it prevents fluid from returning into the drug container.

Figure 5:
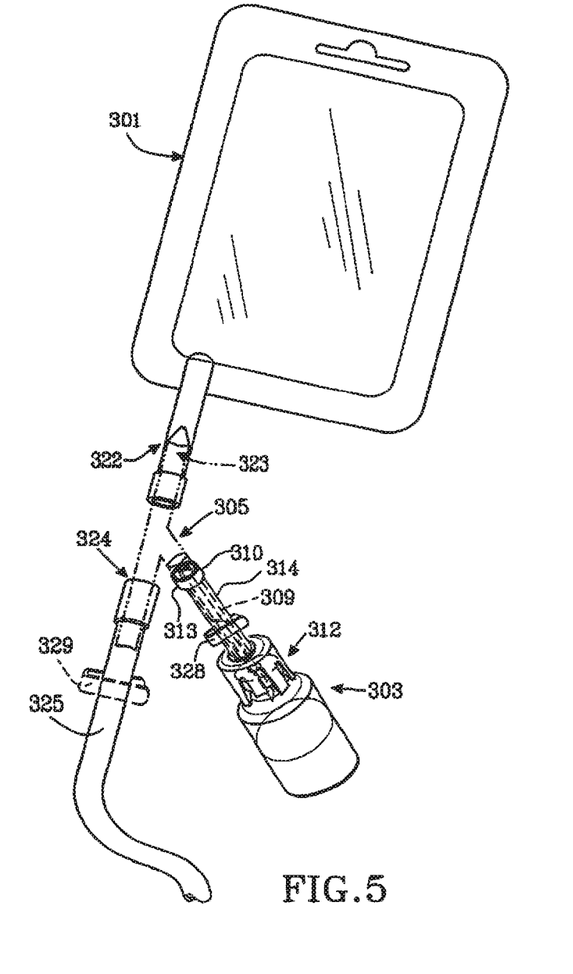
FIG. 5 is perspective view of an alternative embodiment of a fluid transfer assembly according to the invention.

Alternatively, as illustrated in FIG. 5, the cap 312 of the drug container includes a protruding member 314 which forms a second fluid duct between the drug container 303 and the second luer-lock connector 313. The fluid transfer assembly 300 includes a second clamping member 328 for compressing the protruding member 314, thereby closing the second fluid duct and preventing undesired fluid passage between the second luer-lock connector 313 and the drug container 303.

In another alternative embodiment as illustrated in FIG. 5, the fluid container 301 includes a protruding, resilient tube 322. The first luer-lock connector 310 of the inlet port 305 is provided on a hollow spike member 323 designed and arranged to be firmly retained inside the tube 322. This embodiment enables conventional infusion bags to be utilized in the fluid transfer assembly according to the invention.

In still another alternative embodiment of the fluid transfer assembly, in addition to the first luer-lock connector 310, the inlet port 305 also includes an infusion line 325 attached thereto. The fluid transfer assembly 300 also includes a third clamping member 329 for compressing the infusion line 325, thereby preventing undesired fluid passage there through. This embodiment makes it possible to prevent accidental passage of medical substance into the infusion line while transferring the medical substance from the drug container into the infusion fluid container.

In the preferred embodiment of the fluid transfer assembly according to the invention, the inlet port 105, 106 forms a first fluid duct between the fluid container 101 and the first luer-lock connector 110, 111, wherein the fluid barrier 107, 108 is provided inside the first fluid duct. Furthermore, the fluid container 101 is flexible and made of a first polymer material, the first fluid duct is formed by walls 119, 120 made of a second polymer material, the first luer-lock connector 110, 111 is made of a third polymer material, and the fluid barrier 107, 108 is made of a fourth polymer material. As such, the first 101 and second 119, 120 polymer materials are more flexible than the third 110, 111 polymer material, and the fourth polymer material 107, 108 is more brittle than all of the first 101, second 119, 120 and third 110, 111 polymer materials. This preferred choice of materials ensures that the action of the fluid barrier 107 (and 108) between the fluid container and the first luer-lock connector can be eliminated without accidentally breaking other components of the fluid transfer assembly according to the invention.

In a preferred embodiment, the cap 112 includes a protruding member 114 that forms a second fluid duct between the drug container 103 and the second luer-lock connector 113, wherein the fluid barrier 109 is provided inside the second fluid duct. The drug container 103 is made of a rigid material, the protruding member 114 is made of a more flexible material than the second luer-lock connector 113 and the drug container 103, and the fluid barrier 109 is made of a more brittle material than the drug container 103, the protruding portion 114, and the second luer-lock connector 113. In a corresponding way as described above, this preferred choice of materials ensures that the fluid barrier 109 between the drug container and the second luer-lock connector can be eliminated without accidentally breaking any other components of the fluid transfer assembly according to the invention.

In the preferred embodiment of the fluid transfer according to the invention, the drug container 103, 203 is made of glass. However, within the scope of the invention, it also conceivable with embodiments where the drug container is made of other suitable materials, e.g., a rigid polymer material, as long as those material have sufficient chemical resistance and otherwise are suitable from a medical point of view.

In the following, a preferred embodiment and a number of alternative embodiments of a drug container according to the invention will be described in greater detail with particular reference to FIGS. 2, 3 and 4.

The drug container is intended for use in an infusion system including a fluid transfer assembly according to the invention.

The drug container 103, 203, 303 contains a fixed dose of a medical substance 104, 204, 304. In this context, "fixed dose" means that the quantity of medical substance is intended to be transferred to the infusion fluid container in question in its entirety, and that a drug container containing the desired quantity of medical substance has to be selected before administration. The medical substance can be provided either in a fluid state, or advantageously, in the form of a dry powder that is dissolved into a small quantity of infusion fluid from the fluid container connected to the drug container, forming a drug solution which is returned to the infusion fluid container.

According to the invention, the drug container 103, 203, 303 is sealed by a cap 112, 212, 312 exhibiting a luer-lock connector 113, 213, 313 for attachment to a corresponding connector provided on an inlet port of a container for infusion fluid in order to create a luer-lock coupling. This feature enables the drug container to be utilized in a fluid transfer assembly according to the invention. The luer-lock connector of the drug container is preferably a male luer-lock connector when it is intended to interact with an inlet port of a fluid container provided with a female luer-lock connector. In case the drug container is intended to interact with an inlet port exhibiting a male luer-lock connector, it will of course have to exhibit a female luer-lock connector.

In a preferred embodiment of the drug container, the cap 112 includes a protruding member 114 that forms a fluid duct between the drug container 103 and the second luer-lock connector 113. In doing so, a fluid barrier 109 designed and arranged to be ruptured by means of an external force is provided inside the second fluid duct. Preferably, the fluid barrier is designed and arranged to be ruptured by means of an external force exerted by a person by hand. This is also the case with the other fluid barriers included in the fluid transfer assembly according to the invention.

In a preferred embodiment, the drug container 103 includes a neck 115. The cap 112 includes a protruding member 114 attached to the neck 115 by means of an annular capsule member 121. However, as mentioned above, other embodiments are conceivable where the protruding member is permanently attached to the drug container in another suitable way.

In another advantageous embodiment as illustrated in FIG. 4, the drug container 303 includes a neck 315, and the cap 312 includes a protruding member 314 that forms a second fluid duct between the drug container 303 and the second luer-lock connector 313. The cap 312 further includes locking members 316 for grasping the neck 315. This embodiment enables the cap to be permanently attached to a drug vial of a conventional design. Furthermore, the protruding member improves control of the fluid passage out from or into the drug container, since a suitable fluid barrier can be arranged inside the second fluid duct, or the second fluid duct can be blocked or opened by means of applying or removing an external pressure, e.g., as indicated in FIG. 5, by means of a suitable damping member 328 of a type well known per se.

In a preferred embodiment of the drug container as illustrated in FIG. 2, the protruding member 114 encircles a fluid barrier made of a brittle polymer member 109 that can be divided along a weakening line by means of an external force.

In the preferred embodiment, the protruding member 114 forms a fluid duct between the drug container 103 and the luer-lock connector 113, wherein the fluid barrier 109 is provided inside the fluid duct. The drug container 103 is made of a rigid material, the protruding member 114 is made of a more flexible material than the luer-lock connector 113, and the drug container 103, and the fluid barrier 109 is made of a more brittle material than the drug container 103, the protruding portion 114, and the luer-lock connector 113.

In an alternative embodiment of the drug container according to the invention, as illustrated in FIG. 3, the luer-lock connector 213 is attached directly to the cap 212. Advantageously, the luer-lock connector 213 is an integral part of the cap 212. The second luer-lock connector 213 is preferably protected by a removable or pierceable closure 226.

In the alternative embodiment, the drug container 203 advantageously includes a neck 215, wherein the cap 212 includes locking members 216 for grasping the neck 215.

Even more advantageously, the drug container 203 in the alternative embodiment exhibits an opening sealed by a closure 217, wherein the cap 212 exhibits a hollow needle 218 for penetrating the closure 217.

Preferably, the drug container 103, 203 according to the invention is made of glass. However, it is also conceivable with embodiments where the drug container is made of another material, e.g., a suitable rigid polymer material.

In the following, a preferred embodiment and a number of alternative embodiments of a method according to the invention will be described in greater detail, whenever applicable with reference to the attached FIGS. 1-5.

The method is intended for enabling fluid transfer in an infusion system utilizing the fluid transfer assembly according to the invention.

The method includes providing a fluid container 101 containing an infusion fluid 102 and a drug container 103, 203 containing a medical substance 104, 204. The container 101 has at least one inlet port 105, 106 for receiving the medical substance 104, 204 from the drug container 103, 203. The method further includes providing the infusion system with at least one fluid barrier 107, 108 controlling fluid passage between the drug container 103, 203 and the fluid container 101.

The method according to the invention further includes providing the fluid container 101 with a first luer-lock connector 110, 111 on the inlet port 105, 106, providing the drug container 103, 203 with a cap 112, 212 exhibiting a second luer-connector 113, 213, attaching the first luer-lock connector 110, 111 to the second luer-lock connector 113, 213 by means of a luer-lock coupling, applying an external force onto the fluid barrier 107, 109, 108 to open the fluid passage, and creating a positive pressure inside the fluid container 101. According to the invention the method also includes transferring at least part of the positive pressure to the drug container 103, 203 via the fluid passage, and removing the positive pressure from the fluid container 101 in order to initiate transfer of the medical substance 104, 204 from the drug container 103, 203 to the fluid container 101.

In a preferred embodiment, the method further includes rupturing the fluid barrier 107, 108 by means of twisting, bending, or squeezing material portions 119, 120 between the fluid container 101 and the first luer-lock connector 110, 111.

Preferably, the method also includes rupturing another fluid barrier by means of twisting, bending or squeezing material portions 114 between the drug container 103 and the second luer-lock connector 113.

Particularly advantageously, the method further includes providing the drug container 103 with a neck 115, providing the cap 112 with a protruding member 114, providing an annular capsule member 121, and attaching the protruding member 114 to the neck 115 by means of the annular capsule member 121 in a drug container filling line.

Preferably, the method further includes providing the fluid barrier in the form of a brittle polymer member 107, 109, 108 exhibiting at least one weakening line, and dividing the brittle polymer member 107, 109, 108 along the weakening line by means of the external force.

In the preferred embodiment, the method further includes making the fluid container 101 of a flexible first polymer material, forming walls 119, 120 of a second polymer material into a first fluid duct between the fluid container 101 and the first luer-lock connector 110, 111, making the first luer-lock connector 110, 111 of a third polymer material, and making the fluid barrier 107, 108 of a fourth polymer material. Thereby, the method further includes arranging the fluid barrier 107, 108 inside the first fluid duct, selecting the first 101 and second 119, 120 polymer materials to be more flexible than the third 110, 111 polymer material, and selecting the fourth polymer material 107, 108 to be more brittle than all of the first 101, second 119, 120 and third 110, 111 polymer materials.

Preferably, the method further includes making the drug container 103 of a rigid material, including a protruding member 114 on the cap 112 in order to form a second fluid duct between the drug container 103 and the second luer-lock connector 113, and accommodating the fluid barrier 109 inside the second fluid duct. Thereby, the method also includes selecting a more flexible material for the protruding member 114 than for the second luer-lock connector 113 and the drug container 103, and selecting a more brittle material for the fluid barrier 109 than for the drug container 103, the protruding portion 114, and the second luer-lock connector 113.

In an alternative embodiment of the invention, the method further includes providing the drug container 203 with a neck 215, providing the cap 212 with locking members 216, and causing the locking members 216 to grasp the neck 215, thereby attaching the cap 212 permanently to the drug container 203.

In the alternative embodiment, the method advantageously also includes providing the drug container 203 with an opening sealed by a closure 217, providing the cap 212 with a hollow needle 218, and causing the hollow needle 218 to penetrate the closure 217.

Preferably, the method further includes protecting the second luer-lock connector 213 by means of a removable closure 226, and removing the closure before attaching the second luer-lock connector 213 to the first luer-lock connector 111. Alternatively, the method further includes protecting the second luer-lock connector 213 by means of a pierceable closure 226, and piercing the closure 226 when attaching the second luer-lock connector 213 to the first luer-lock connector 111. This, of course, requires that the pierceable closure is made of material which will not release any loose particles into the luer-lock coupling or the fluid passage. The skilled person, having read this description, should be able to find such a suitable material without any extensive work.

The method according to the invention preferably also includes to make the drug container 103, 203 of glass or a rigid polymer material.

As used herein, the expression "drug container" refers to a container for medical substance which is leakage-proof and otherwise suitable for the purpose in question. Preferably, the "drug container" utilized in the assembly according to the invention has only one opening which is sealed by a closure or cap, and is made of a solid, rigid and inflexible material, such as glass or rigid polymer material. Furthermore, it is preferred that the drug container has no displaceable bottom, flexible walls, or the like, which will prevent the creation of the positive pressure which is needed in order to empty the medical substance into the infusion fluid In the Interacting fluid container.

As used herein, the expression "permanent attachment" means that the components in question, in their normal, intended use, cannot be disengaged without the use of excessive force.

In the foregoing description, the present invention has been described in connection with a few specific embodiments and with reference to the attached drawings. However, the present invention is by no means strictly confined to these embodiments or to what is shown in the drawings, but the scope of the invention is defined in the following claims.

Accordingly, as illustrated in FIG. 1, the method according to the invention can further include making the walls 119 of the inlet port 105 of a flexible material, forming a first fluid duct between the fluid container 101 and the first luer-lock connector 110 inside the flexible material, and providing a first clamping member 127 for compressing the walls 119, thereby closing the first fluid duct and preventing undesirable fluid passage between the fluid container 101 and the first luer-lock connector 110.

In still another embodiment, illustrated in FIG. 5, the method can include providing the cap 312 with a protruding member 314 that forms a second fluid duct between the drug container 303 and the second luer-lock connector 313, and providing a second clamping member 328 for compressing the protruding member 314, thereby closing the second fluid duct and preventing undesirable fluid passage between the second luer-lock connector 313 and the drug container 303.

Furthermore, the method can also include providing the fluid container 301 with a protruding, resilient tube 322, providing a hollow spike member 323 for the first luer-lock connector 310, and inserting the hollow spike member 323 into the resilient tube 322, and/or attaching an infusion line 325 to the inlet port 305, in addition to the first luer-lock connector 310, and providing a third clamping member 329 for compressing the infusion line 325, thereby preventing undesirable fluid passage there through.

While only certain preferred embodiments of the invention have been illustrated and described, it is realized that several variations and modifications within the scope of the enclosed claims can occur.

What is claimed is:

1. A drug container for use in an infusion system, said drug container comprising:
    a fixed dose of a medical substance, and
    a cap for sealing said drug container, said cap further comprising:
        a luer-lock connector for attachment to a corresponding connector provided on an inlet port of a container for infusion fluid, thereby creating a luer-lock coupling,
        a protruding member forming a fluid duct between said drug container and said luer connector, and
        a fluid barrier provided inside said fluid duct,
    wherein said drug container comprises a rigid material, said protruding member comprises a more flexible material than said luer-lock connector and said drug container, and said fluid barrier is made of a more brittle material than said drug container, said protruding member, and said luer-lock connector.

2. The drug container according to claim 1, wherein said luer-lock connector is attached directly to said cap.

3. The drug container according to claim 1, wherein said luer-lock connector is integral with said cap.

4. The drug container according to claim 1, further comprising a removable closure for protecting said luer-lock connector.

5. The drug container according to claim 1, further comprising a pierceable closure for protecting said luer-lock connector.

6. The drug container according to claim 1, said drug container further comprising a neck, and said protruding member is able to be attached to said neck by an annular capsule member.

7. The drug container according to claim 1, said drug container further comprising an opening sealed by a closure, and said cap further comprising a hollow needle for penetrating said closure.

8. The drug container according to claim 1, wherein said drug container is made from the group consisting of glass and a rigid polymer material.

* * * * *